Figure 1:
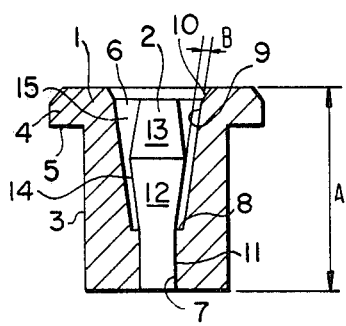

United States Patent [19]

Scholer

[11] 4,341,312
[45] Jul. 27, 1982

[54] HOLDER FOR SMALL INSTRUMENTS SUCH AS DENTAL INSTRUMENTS

[76] Inventor: Arno Scholer, Riederbachweg 7, 3292 Busswil, Switzerland

[21] Appl. No.: 143,777

[22] Filed: Apr. 25, 1980

[30] Foreign Application Priority Data

Apr. 30, 1979 [CH] Switzerland ............... 4023/79

[51] Int. Cl.³ .................... A61G 1/14; A47F 7/00
[52] U.S. Cl. .................... 211/60 T; 433/77; 211/69
[58] Field of Search ............... 211/60 T, 69; 206/368, 206/369, 370, 379; 433/77

[56] References Cited

U.S. PATENT DOCUMENTS 3,298,532  1/1967  Wilcke ..................... 211/60 T
4,253,830  3/1981  Kazen ..................... 211/69

Primary Examiner—Reinaldo Machado
Attorney, Agent, or Firm—Young & Thompson

[57] ABSTRACT

A holder for small instruments such as dental instruments, comprises an inner member and an outer member both of which are figures of rotation. The outer member has a conical recess in its upper portion and a cylindrical recess in its lower portion. The inner member has a cylindrical lower portion by which it is secured in the cylindrical recess of the outer member, and has two truncated conical portions one above the other, the lower of which forms a relatively narrow conical recess with the outer member and the upper of which is of reverse inclination to the inclination of the conical recess of the outer member so as to provide a tapered entrance recess into the lower recess. The lower recess forms an angle of about 7.5° with the axis of the holder.

7 Claims, 2 Drawing Figures

HOLDER FOR SMALL INSTRUMENTS SUCH AS DENTAL INSTRUMENTS

The present invention relates to holders for small instruments such as dental instruments, that is, dental polishing instruments, drills, root canal instruments and endodontic accessories.

In the past, such small instruments have been held in receptacles in which they could be positioned horizontally in individual recesses or vertically or obliquely in relatively large cylindrical bores. Such holders are disclosed for example in the publication of K. Kimmel entitled "Rotierende Instrumente fur Klinik, Praxis und Labor", Hager und Meisinger GmbH, Dusseldorf, 1977.

However, the holders known thus far take up a great deal of space, are cumbersome and make it difficult to see the instruments.

The present invention overcomes the difficulties of the known devices in this field, by providing a holder in which the instruments can be held individually in side-by-side relationship in a circular configuration. When the instruments are deposited in the holder, they slide between converging walls of an inlet portion of an annular recess and into a relatively narrow conical recess having parallel walls disposed at an angle of about 7.5° to the axis of the holder. The width of the relatively narrow lower portion of the recess is preferably not much greater than the diameter of the shank of the instruments to be held, the height of the holder being desirably about half the length of the instruments to be held.

Figure 2:
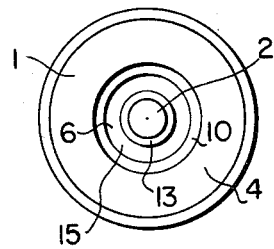

Other features and advantages of the pesent invention will become apparent from a consideration of the following description, taken in connection with the accompanying drawing, in which:

FIG. 1 is an elevational view partly in cross section, showing a holder according to the present invention; and FIG. 2 is a top plan view of the holder shown in FIG. 1.

Referring now to the drawing in greater detail, there is shown a holder according to the present invention, which is in two parts 1 and 2 each of which is a figure of rotation about the axis of the holder.

The outer part 1 has a cylindrical outer surface 3 that terminates upwardly in an outwardly extending support flange 4 whose undersurface 5 lies in a plane perpendicular to the axis of the holder. The diameter of the outer part is such as to be received in an opening of a support surface such as a table or drawer, on which the holder will be supported by the mentioned flange 4. It is of course contemplated that more than one such holder can be provided on the support.

In its interior, the outer part 1 has a central opening 6 whose lower portion 7 is cylindrical and of the least diameter of any portion of the central opening. That cylindrical portion terminates upwardly in a radially outwardly extending step 8 by which the diameter of the central opening enlarges; and there follows upwardly a conical portion 9 of the central opening whose side walls flare outwardly upwardly at an angle of about 7.5° to the axis of the holder. At the top of this conical side wall, a chamfer 10 of greater angle can be provided if desired.

The other portion of the holder is an inner part 2, that terminates downwardly in a cylindrical portion 11 by which it is secured in the corresponding cylindrical part 7 of the central opening of outer part 1; and above this lower cylindrical portion 11 of part 2 are arranged sequentially two truncated conical portions 12 and 13, the lower of which has the same taper as the conical side walls of the central recess 6 of outer part 1 but lesser diameter, and the other of which has an opposite taper so that it converges upwardly.

The conical internal side wall 9 of outer part 1 and the matching but spaced conical outer surface 12 of inner part 2 are thus parallel to each other and spaced apart by a distance which is adapted to the article to be held in the holder, e.g. a little greater than the diameter of the shanks of the tools to be held.

There is thus provided between outer part 1 and inner part 2, what can be considered to be a pair of recesses 14 and 15 that are superposed, annular and coaxial. The upper recess 15 has a thickness tha decreases downwardly and is defined between two conical surfaces 9 and 13 of opposite inclination. The lower recess 14 is of substantially uniform thickness and is defined between two conical surfaces 9 and 12 that are parallel to each other and terminates downwardly in a radial step 8 which can be formed either on outer part 1 or on inner part 2 but is preferably formed on outer part 1 as shown.

The holder according to the present invention is used merely by inserting the instruments, handle down, between the parts 1 and 2, whereupon they are automatically guided to the lower end of the recess 14 between these parts and held at about the same angle, namely, 7.5°, that characterizes the lower portion of the recess. Thus, the upper portions of the instruments will diverge from each other much in the manner of a conical fan pattern, making the instruments easy to deposit in the holder and remove from the holder. At the same time, the annular configuration of the recess in which they are held, with its parallel walls in the lower portion thereof, ensures that the instruments cannot become canted and jammed in the holder. It is possible by this arrangement to accommodate in the least space a large number of individual instruments in a manner that will be readily visible and convenient to use.

It is preferred that the material of the holder be aluminum, as this withstands the heat of autoclaving and permits color coding by anodizing.

Although the present invention has been described and illustrated in connection with a preferred embodiment, it is to be understood that modifications and variations may be resorted to without departing from the spirit of the invention, as those skilled in this art will readily understand. Such modifications and variations are considered to be within the purview and scope of the present invention as defined by the appended claims.

What is claimed is:

1. A holder for small instruments, comprising a holder body having therein an annular recess, the recess having an upper portion defined between side walls that converge downwardly and a lower portion defined between parallel side walls.

2. A holder as claimed in claim 1, said parallel side walls being upwardly opening conical surfaces.

3. A holder as claimed in claim 2, said converging side walls comprising an upwardly opening conical outer wall and an upwardly converging conical inner wall.

4. A holder as claimed in claim 3, the outer walls defining said upper and lower portions comprising a single cone.

5. A holder as claimed in claim 1, which is in two parts comprising an inner part and an outer part both of which are figures of revolution, said inner and outer parts being fixedly secured together at their lower ends and defining between them said recess above their lower ends.

6. A holder as claimed in claim 5, in which a radial step is provided on one of said parts to define the bottom of said lower portion.

7. A holder as claimed in claim 1, and a radially outwardly extending flange at the top of said body for mounting said body in a support.

* * * * *